United States Patent [19]

Shribbs et al.

[11] Patent Number: 5,627,131
[45] Date of Patent: May 6, 1997

[54] HERBICIDAL COMPOSITIONS OF 4-BENZOYLISOXAZOLE AND ANTIDOTES THEREFOR

[75] Inventors: John M. Shribbs, Petaluma; David L. Lee, Pleasant Hill, both of Calif.

[73] Assignee: Zeneca Limited, London, England

[21] Appl. No.: 370,070

[22] Filed: Jan. 9, 1995

[51] Int. Cl.$^6$ .................................................. A01N 25/32
[52] U.S. Cl. ........................ 504/105; 504/107; 504/108; 504/112
[58] Field of Search .................................. 504/107, 108, 504/112, 105

[56] References Cited

U.S. PATENT DOCUMENTS

| | | | |
|---|---|---|---|
| 4,021,224 | 5/1977 | Pallos et al. | 71/88 |
| 4,021,229 | 5/1977 | Ameklev et al. | 71/100 |
| 4,230,874 | 10/1980 | Pallos et al. | 560/12 |
| 4,276,078 | 6/1981 | Pallos et al. | 71/88 |
| 4,938,796 | 7/1990 | Buren et al. | 71/98 |
| 5,201,933 | 4/1993 | Miller et al. | 504/104 |
| 5,371,063 | 12/1994 | Cramp et al. | 504/270 |
| 5,371,064 | 12/1994 | Cramp et al. | 504/271 |
| 5,374,606 | 12/1994 | Cramp et al. | 504/270 |

FOREIGN PATENT DOCUMENTS

| | | |
|---|---|---|
| 0418175 | 3/1991 | European Pat. Off. . |
| 487357 | 5/1992 | European Pat. Off. . |
| 0496630 | 7/1992 | European Pat. Off. . |
| 0496631 | 7/1992 | European Pat. Off. . |
| 0527036 | 2/1993 | European Pat. Off. . |
| 0527037 | 2/1993 | European Pat. Off. . |
| 0625505 | 11/1994 | European Pat. Off. . |
| 92/10095 | 6/1992 | WIPO . |

*Primary Examiner*—Allen J. Robinson
*Assistant Examiner*—B. Bembenick
*Attorney, Agent, or Firm*—Marian T. Thomson

[57] ABSTRACT

Herbicidal compositions containing 4-benzoylisoxazole compounds and antidotal compounds therefor to reduce injury to various crops, particularly corn, from the phytotoxic effects of 4-benzoylisoxazole herbicides when used alone or in combination with additional pesticidally active ingredients. Methods for reducing phytotoxicity or injury to crop plants, particularly corn crops, due to 4-benzoylisoxazole herbicides are also described.

4 Claims, No Drawings

HERBICIDAL COMPOSITIONS OF 4-BENZOYLISOXAZOLE AND ANTIDOTES THEREFOR

FIELD OF THE INVENTION

This invention relates to herbicide compositions and methods of use and, more particularly, to certain herbicidal compositions comprising 4-benzoylisoxazole or 2-cyano-1,3-dione compounds and antidotes therefor which are useful as herbicides.

BACKGROUND OF THE INVENTION

An herbicide is a compound which adversely controls or modifies plant growth, e.g., killing, retarding, defoliating, desiccating, regulating, stunting, tillering, stimulating and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: preplant incorporation into the soil; in-furrow application to seeds and surrounding soil; pre-emergence surface treatment of seeded soil; post-emergence treatment of the plant and soil; and preplant seed treatment.

A manufacturer of an herbicide generally recommends a range of application rates and concentrations calculated to maximize weed control. The range of rates varies from approximately 0.01 to 50 pounds per acre (0.0111 to 56 kilograms per hectare [kg/ha]), and is usually in the range of from 0.1 to 25 pounds per acre (0.112 to 28 kg/ha). The term "herbicidally effective amount" describes an amount of an herbicide compound which adversely controls or modifies plant growth. The actual amount used depends upon several considerations, including particular weed susceptibility and overall cost limitations.

An important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which infest the locus of the crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See, for example, U.S. Pat. Nos. 4,021,224, 4,021,229 and 4,230,874.

Identification of an antidote which safens an herbicide in crops is a highly complicated task. The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species by the herbicide, and reduced or non-phytotoxicity to the cultivated crop species. The term "antidotally effective amount" describes an amount of an antidote compound which counteracts to some degree a phytotoxic response of a beneficial crop to an herbicide.

4-benzoylisoxazole and 2-cyano-1,3-dione compounds have been found to be very effective herbicides with broad general herbicidal activity against broad-leafed and grass weeds by pre- and/or post-emergence application. The method of controlling vegetation with these compounds comprises applying an herbicidally effective amount of the compounds, usually with an inert carrier or diluent, to the area where herbicidal control is desired. However, the herbicidal 4-benzoylisoxazole and 2-cyano-1,3-dione compounds have been found in some instances to adversely affect or interfere with the cultivation of crop plants, especially corn crops. Therefore, the effective use of these herbicides for controlling weeds in the presence of such crops is further enhanced by, or may require in many instances, the addition of an antidotally effective amount of a compound, which is antidotally effective with the herbicide.

It has now been discovered that certain compounds when used in an antidotally effective amount are effective antidotes for the protection of crops, especially corn crops, from adverse herbicidal injury or the reduction of adverse herbicidal injury caused by the use of an herbicidally effective amount of a 4-benzoylisoxazole or 2-cyano-1,3-dione compound. Therefore, it is an object of the present invention to provide compositions of 4-benzoylisoxazole and 2-cyano-1,3-dione herbicides in combination with antidotes therefor, which compositions are useful to reduce injury to crops, especially corn, due to phytotoxicity of these herbicides.

SUMMARY OF THE INVENTION

The present invention relates to herbicidal compositions comprising herbicidal 4-benzoylisoxazole or 2-cyano-1,3-dione compounds and antidotal compounds therefor to reduce injury to various crops, particularly corn, from the phytotoxic effects of such 4-benzoylisoxazole or 2-cyano-1,3-dione herbicides when used alone or in combination with other compounds as co-herbicides.

More particularly, the invention relates to a composition comprising:

(a)
  (i) an herbicidal 4-benzoylisoxazole, or an agriculturally acceptable salt thereof; or
  (ii) an herbicidial 2-cyano-1,3-dione compound, or an agriculturally acceptable salt thereof; and
(b) an antidotally effective amount of an antidote compound which is antidotally effective with the herbicidal compound (a).

The invention further relates to methods for reducing phytotoxicity or injury to crop plants, particularly corn crops, due to a herbicidal 4-benzoylisoxazole or 2-cyano-1,3-dione compound, or salt thereof, by applying an antidotally effective amount of an antidote compound to the soil, crop or crop seed.

DETAILED DESCRIPTION OF THE INVENTION

4-Benzoylisoxazole herbicide compounds useful in the present invention are described in U.S. Pat. Nos. 5,371,063, 5,371,064 and 5,374,606 and in European Patent Publication Nos. 0 418 175, 0 487 357, 0 527 036 and 0 527 037, the disclosures of which are incorporated herein by reference thereto. Herbicidal 4-benzoylisoxazole compounds for use in this invention may be prepared by the methods described in the aforementioned patent publications, or by the application and adaptation of known methods used or described in the chemical literature.

Many herbicidal 4-benzoylisoxazole compounds useful in this invention fall within the general formula

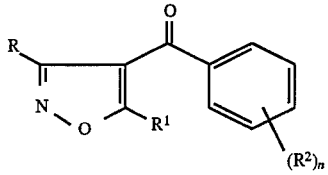

(I)

wherein,

R represents a hydrogen atom; a halogen atom; a straight- or branched-chain alkyl, alkenyl or alkynyl group containing up to six carbon atoms which is optionally substituted by one or more halogen atoms; a cycloalkyl group containing from 3 to 6 carbon atoms optionally substituted by one or more groups —$R^5$, one or more halogen atoms or a group —$CO_2R^3$; or a group selected from —$CO_2R^3$, —$COR^5$, cyano, nitro, or —$CONR^3R^4$;

$R^1$ represents a straight- or branched-chain alkyl, alkenyl or alkynyl group containing up to six carbon atoms which is optionally substituted by one or more halogen atoms; or a cycloalkyl group containing from three to six carbon atoms optionally substituted by one or more groups $R^5$ or one or more halogen atoms;

$R^2$ represents a halogen atom; a straight- or branched-chain alkyl, alkenyl, alkynyl or alkoxy group containing up to six carbon atoms which is optionally substituted by one or more groups —$OR^5$ or one or more halogen atoms; or a group selected from nitro, cyano, —$CO_2R^3$, —$S(O)_pR^6$, —$O(CH_2)_mOR^5$, —$COR^5$, —$NR^{61}R^{62}$, —$N(R^8)SO_2R^7$, —$OR^5$, —$OSO_2R^7$, —$SO_2NR^3R^4$, —$CONR^3R^4$, —$CSNR^3R^4$ and —$(CR^9R^{10})_t$—$S(O)_qR^7$;

n represents an integer from one to five; when n is greater than one, the groups $R^2$ may be the same or different;

$R^3$ and $R^4$ each independently represents a hydrogen atom; or a straight- or branched-chain alkyl group containing up to six carbon atoms which is optionally substituted by one or more halogen atoms;

$R^5$ represents a straight- or branched-chain alkyl group containing up to six carbon atoms which is optionally substituted by one or more halogen atoms; a straight- or branched-chain alkenyl or alkynyl group containing from three to six carbon atoms which is optionally substituted by one or more halogen atoms; or phenyl optionally substituted by from one to five groups $R^2$ which may be the same or different;

$R^6$, $R^{61}$ and $R^{62}$, which may be the same or different, each represents a straight- or branched-chain alkyl group containing up to six carbon atoms which is optionally substituted by one or more halogen atoms; or phenyl optionally substituted by from one to five groups $R^2$ which may be the same or different;

$R^7$ represents a straight- or branched-chain alkyl group containing up to six carbon atoms which is optionally substituted by one or more halogen atoms; phenyl optionally substituted by from one to five groups $R^2$ which may be the same or different; or a halogen atom;

$R^8$ represents a hydrogen atom; a straight- or branched-chain alkyl, alkenyl or alkynyl group containing up to ten carbon atoms which is optionally substituted by one or more halogen atoms; a cycloalkyl group containing from three to six carbon atoms; phenyl optionally substituted by from one to five groups which may be the same or different selected from halogen, nitro, cyano, $R^5$, —$S(O)_pR^5$ and —$OR^5$; or a group selected from —$SO_2R^6$ and —$OR^5$;

$R^9$ and $R^{10}$, which may be the same or different, each represents a hydrogen atom; a straight- or branched-chain alkyl group containing up to six carbon atoms which is optionally substituted by one or more halogen atoms; or phenyl optionally substituted by from one to five groups $R^2$ which may be the same or different;

$R^{51}$ and $R^{52}$, which may be the same or different, each represents a hydrogen atom; or a straight- or branched-chain alkyl group containing up to six carbon atoms which is optionally substituted by one or more halogen atoms;

p represents zero, one or two;

q represents zero, one or two;

m represents one, two or three;

t represents an integer from one to four; when t is greater than one the groups —$CR^9R^{10}$— may be the same or different;

or an agriculturally acceptable salt thereof which possesses herbicidal properties.

In certain cases, the groups R to $R^{10}$, $R^{51}$, $R^{52}$, $R^{61}$ and $R^{62}$ may give rise to optical and/or stereoisomerism. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable acid addition salts, formed by compounds of formula (I) containing an amino group, include salts with inorganic acids, for example, hydrochlorides, sulphates, phosphates and nitrates and salts with organic acids, for example, acetic acid. Suitable salts formed by compounds of formula (I) which are acidic, i.e., compounds containing one or more carboxy groups, with bases include alkali metal (e.g. sodium and potassium) salts, alkaline earth metal (e.g. calcium and magnesium) salts, ammonium and amine (e.g. diethanolamine, triethanolamine, octylamine, dioctylmethylamine and morpholine) salts.

One preferred class of compounds of formula (I) are those having the formula

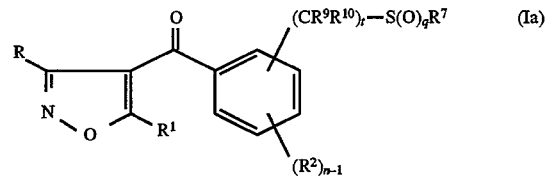

(Ia)

wherein R, $R^1$, $R^2$, $R^7$, $R^9$, $R^{10}$, n, q and t have the meanings set forth above.

In a further preferred embodiment where n is greater than one, the benzoyl ring of the compounds of formula (Ia) is 2,4-disubstituted or 2,3,4-trisubstituted. Compounds of formula (Ia) in which n is greater than one and the benzoyl ring of the compound of formula (Ia) is 2,3-disubstituted are also preferred.

A further preferred class of compounds of formula (Ia) are those wherein: R is hydrogen or —$CO_2Et$; $R^1$ is cyclopropyl; $R^2$ is a halogen atom or a group selected from —$CF_3$, —$S(O)_pMe$ and —OMe; n is one, two or three; t is one; $R^7$ is a straight- or branched-chain alkyl or alkenyl group containing up to four carbon atoms optionally substituted by from one to three fluorine atoms, or is phenyl; $R^9$ is hydrogen or methyl; $R^{10}$ is hydrogen; and p and q, which may be the same or different, each is zero, one or two.

Another preferred class of compounds of formula (I) are compounds having the formula

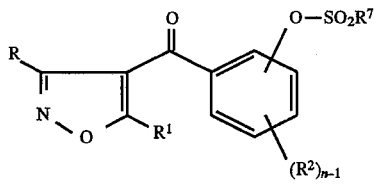

(Ib)

wherein R, $R^1$, $R^2$, $R^7$, and n have the meanings set forth above.

A further preferred class of compounds of formula (Ib) are those wherein R is hydrogen; $R^1$ is ethyl or cyclopropyl; $R^2$ is halogen; n is one or two; and $R^7$ is methyl, ethyl or —NMe$_2$.

Another preferred class of compounds of formula (I) are those having the formula

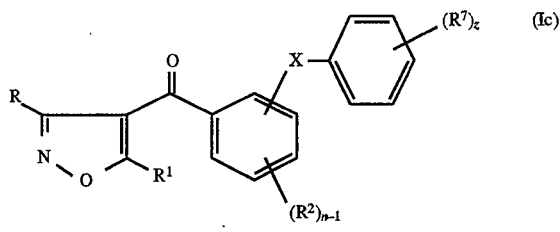

(Ic)

wherein X is oxygen or —S(O)$_q$—; z is zero or an integer from one to five; and R, $R^1$, $R^2$, $R^7$ and n have the meanings set forth above.

A further preferred class of compounds of formula (Ic) are those wherein one of the substituents of the benzoyl ring is in the 2-position.

Other preferred compounds of formula (Ic) are those wherein the 5- and/or 6-position of the benzoyl ring is unsubstituted, more especially preferred both the 5- and 6-positions are unsubstituted.

A further preferred class of compounds of formula (Ic) are those wherein $R^1$ is a cyclopropyl group; $R^2$ is halogen or a group selected from methyl, trifluoromethyl, methoxy and —S(O)$_p$R$^6$; n is two or three; X is —S(O)$_q$—; $R^7$ is halogen or a group selected from methyl, trifluoromethyl, nitro and —OR$^5$; $R^5$ is methyl or ethyl; and $R^6$ is methyl.

A further preferred class of compounds of formula (I) are those having the formula

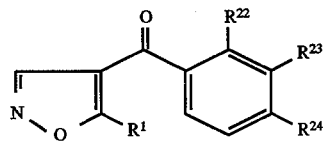

(Id)

wherein:

$R^1$ is a methyl, ethyl, isopropyl, cyclopropyl or 1-methylcyclopropyl group;

$R^{22}$ is a chlorine, bromine or fluorine atom, or a straight- or branched-chain alkyl or alkoxy group containing up to four carbon atoms;

$R^{23}$ is a hydrogen, chlorine, bromine or fluorine atom; a group selected from $R^5$, —CO$_2$R$^5$ and —OR$^5$; or a straight- or branched-chain alkyl or alkoxy group containing up to four carbon atoms substituted by —OR$^5$;

$R^{24}$ is —S(O)$_p$R$^6$;

$R^5$ is a straight- or branched-chain alkyl group containing up to four carbon atoms which is optionally substituted by one or more halogen atoms;

$R^6$ is a methyl or ethyl group; and p is zero, one or two.

An especially preferred class of compounds of formula (I) have the formula

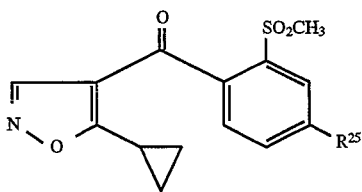

(Ie)

wherein $R^{25}$ is chlorine, bromine or trifluoromethyl.

Because of their herbicidal properties, compounds of formula (I) wherein $R^1$ is substituted or unsubstituted cyclopropyl are particularly preferred for use in the herbicidal compositions of the present invention. The following compounds are among the most preferred 4-benzoylisoxazole compounds for use in the present invention: 5-cyclopropyl-4-[2-chloro-3-ethoxy-4-(ethylsulfonyl)benzoyl]isoxazole; 4-(4-chloro-2-methylsulphonylbenzoyl)-5-cyclopropylisoxazole; 5-cyclopropyl-4-(2-methylsulphonyl-4-trifluoromethylbenzoyl)isoxazole; and 4-(4-bromo-2-methylsulphonylbenzoyl)-5-cyclopropylisoxazole.

2-Cyano-1,3-dione herbicide compounds useful in the present invention are described in European Patent Publication Nos. 0 496 630 and 0 496 631, the disclosures of which are incorporated herein by reference thereto. Herbicidal 2-cyano-1,3-dione compounds for use in this invention may be prepared by the methods described in the aforementioned patent publications, or by the application and adaptation of known methods used or described in the chemical literature.

Many of the herbicidal 2-cyano-1,3-dione compounds useful in the present invention fall within the general formula

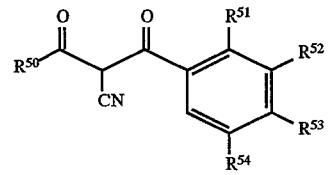

(II)

wherein:

$R^{50}$ is a straight- or branched-chain alkyl group containing up to six carbon atoms which is optionally substituted by one or more halogen atoms which may be the same or different; or a cycloalkyl group containing from three to six carbon atoms which is optionally substituted by one or more groups selected from $R^{55}$ and one or more halogen atoms which may be the same or different;

one of $R^{51}$ and $R^{53}$ is —S(O)$_r$R$^{56}$ and the other of $R^{51}$ and $R^{53}$ is a halogen atom; a hydrogen atom; a straight- or branched-chain alkyl group containing up to six carbon atoms which is substituted by —OR$^{55}$; —R$^{55}$; nitro; cyano; —SR$^{55}$; —OR$^{55}$; —O(CH$_2$)$_s$OR$^{55}$; or —CO$_2$R$^{55}$;

$R^{52}$ and $R^{54}$, which may be the same or different, each is a halogen atom; a hydrogen atom; a straight- or branched-chain alkyl group containing up to six carbon atoms which is substituted by —OR$^{55}$; —R$^{55}$; nitro; cyano; —OR$^{55}$; —O(CH$_2$)$_s$OR$^{55}$; or —CO$_2$R$^{55}$;

$R^{55}$ and $R^{56}$, which may be the same or different, each is a staight- or branched-chain alkyl group containing up to six carbon atoms which is optionally substituted by one or more halogen atoms which may be the same or different;

s is an integer from 1 to 3; and r is zero, 1 or 2;

and where the compounds exist in enolic tautomeric forms, agriculturally acceptable salts thereof, which possess valuable herbicidal properties.

Compounds of formula (II) may exist in enolic tautomeric forms that may give rise to geometric isomers around the enolic double bond. Furthermore, in certain cases, the substituents $R^{50}$, $R^{51}$, $R^{52}$, $R^{53}$, $R^{54}$, $R^{55}$ and $R^{56}$ may contribute to optical isomerism and/or stereoisomerism. All such forms are embraced within 2-cyano-1,3-dione compounds useful in the present invention.

This invention embodies a two-part herbicidal system comprised of (a) a 4-benzoylisoxazole or 2-cyano-1,3-dione herbicide as described hereinabove and (b) an effective antidote therefor. It has been found that such antidote compounds can be selected from a wide range of chemical substances that have been found to be effective as herbicide antidotes for the above-described 4-benzoyl-isoxazole herbicides. The preferred compositions of this invention may include any one or more of such antidotes with the herbicides. The variety of crops on which the above-described herbicides is useful can be significantly broadened by the use of an antidote to protect one or more crops from injury therefrom and render the composition more selective against weeds. Some of the more important types of antidotes are amides of haloalkanoic acids, aromatic oxime derivatives, thiazole carboxylic acids and derivatives, and 1,8-naphthalic anhydride.

Preferably, the compositions of the present invention comprise an antidotally-effective amount of
(i) a compound of the formula

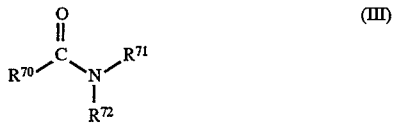

(III)

wherein $R^{70}$ can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonalkyl; alkylthioalkyl; haloalkylcarbonyloxyalkyl; alkoxycarboalkyl; haloalkenylcarbonyloxyalkyl; hydroxyhaloalkyloxyalkyl; hydroxyalkylcarboalkyloxyalkyl; hydroxyalkyl; alkoxysulfonoalkyl; furyl; thienyl; alkyldithiolenyl; thienalkyl; phenyl; substituted phenyl wherein the substitutents can be selected from halogen, alkyl, haloalkyl, alkoxy, carbamyl, nitro, carboxylic acids and their salts, and haloalkylcarbamyl; phenylalkyl; phenylhaloalkyl; phenylalkenyl; substituted phenylalkenyl wherein the substituents can be selected from halogen, alkyl, alkoxy, and halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; and alkynylcarbamylbicycloalkenyl;

$R^{71}$ and $R^{72}$, which may be the same or different, are selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substitutents can be selected from alkyl, halogen, haloalkyl, alkoxy, haloalkylamido, phthalamido, hydroxy, alkylcarbamyloxy, alkenylcarbamyloxy, alkylamido, haloalkylamido and alkylcarboalkenyl; phenylsulfonyl; substituted phenylalkyl wherein said substituents can be selected from halogen or alkyl; dioxyalkylene; halophenoxyalkylamido-alkyl; alkylthiodiazolyl; piperidyl; piperidylalkyl; dioxolanylalkyl; thiazolyl; alkylthiazolyl; benzothiazolyl; halobenzothiazolyl; furyl; alkyl-substituted furyl; furylalkyl; pyridyl; alkylpyridyl; alkoxazolyl; tetrahydrofurylalkyl; 3-cyano- thienyl; alkyl substituted thienyl; 4,5-polyalkylene thienyl; α-haloalkylacetamidophenylalkyl; α-haloalkylacetamidonitrophenylalkyl; α-haloalkylacetamidohalophenylalkyl; and cyanoalkenyl; or $R^{71}$ and $R^{72}$ when taken together can form a structure consisting of piperidinyl; alkylpiperidinyl; pyridyl; di- or tetrahydropyridinyl; alkyltetrahydropyridyl; morpholyl; azabicyclononyl; diazacycloalkanyl; benzoalkylpyrrolidinyl; oxazolidinyl; perhydrooxazolidinyl; alkyloxazolidinyl; furyloxazolidinyl; thienyloxazolidinyl; pyridyloxazolidinyl; pyrimidinyloxazolidinyl; benzooxazolidinyl; $C_{3-7}$ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1, 4-diazepinyl; quinolinyl; isoquinolinyl; dihydro-, tetrahydro- or perhydroquinolyl or isoquinolyl; indolyl or di- or perhydroindolyl; and which combined $R^{71}$ and $R^{72}$ members can be substituted with those independent $R^{71}$ and $R^{72}$ radicals enumerated above; or
(ii) one of the following compounds:
α-[(cyanomethoxy)imino]benzeneacetonitrile;
α-[(1,3-dioxolan-2-ylmethoxy)imino]-benzeneacetonitrile;
O-[3-dioxolan-2-ylmethyl]-2,2,2-trifluoromethyl-4'-chloroacetophenone oxime;
benzenemethamine, N-[4-(dichloromethylene)-1,3-diotholan-2-ylidene]-α-methyl, hydrochloride;
diphenylmethoxy acetic acid, methyl ester;
1,8-naphthalic anhydride;
cloquintocet;
4,6-dichloro-2-phenylpyrimidine;
2-chloro-N-[1-(2, 4, 6-trimethylphenyl)ethenyl] acetamide; and
ethylene glycol acetal of 1,1-dichloroacetone.

Antidotal amides of haloalkanoic acids of formula (III), which include those in which the nitrogen forms a portion of a heterocyclic ring with substituents, are described in a number of publications such as U.S. Pat. Nos. 4,021,224, 4,256,481, 4,294,764, and 5,201,933 and British Patent 1,521,540. U.S. Pat. No. 4,021,224 contains a broad disclosure of such types of compounds and indicates a great many possibilities for mono- or di-substitution on the nitrogen atom.

One group of preferred antidotal compounds includes those according to formula (III) wherein $R^{70}$ is $C_{1-3}$ haloalkyl, $R^{71}$ and $R^{72}$ are independently $C_{2-4}$ alkenyl or haloalkenyl or 2,3-dioxolan-2-yl-methyl and $R^{71}$ and $R^{72}$ when combined form a $C_{4-10}$ saturated or unsaturated heterocyclic ring containing O, S and/or N atoms and which may be substituted with $C_{1-5}$ alkyl, haloalkyl, alkoxy, alkoxyalkyl or haloacyl groups. The preferred haloalkyl $R^{70}$ member in formula (III) is dichloromethyl. Preferred species in this group of antidotal compounds are N,N-diallyl-dichloroacetamide and N-(2-propenyl)-N-(1,3-dioxolanylmethyl)dichloroacetamide.

Still more preferred antidotal compounds according to formula (III) is a group of substituted 1,3-oxazolidinyl or thiazolidinyl dichloroacetamides having the formula

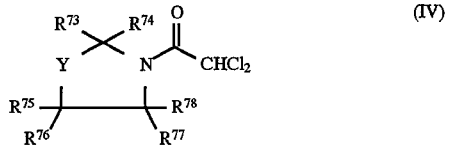

wherein

Y is oxygen or sulfur;

$R^{73}$, $R^{74}$, $R^{75}$, $R^{76}$, $R^{77}$ and $R^{78}$ are independently hydrogen; $C_{1-4}$ alkyl, alkylol, haloalkyl or alkoxy; $C_{2-6}$ alkoxyalkyl; $C_{1-4}$ alkylthio($C_{1-4}$)alkyl; $C_{1-4}$ alkylsulfonylmethyl; a bicyclic hydrocarbon radical having up to 10 carbon atoms; phenyl; or a saturated or unsaturated heterocyclic radical having $C_{4-10}$ ring atoms and containing O, S and/or N atom(s); wherein the phenyl and heterocyclic radicals are optionally substituted with one or more $C_{1-4}$ alkyl, $C_{1-4}$ haloalkyl, $C_{1-4}$ alkoxy, $C_{2-6}$ alkoxyalkyl, halogen or nitro radicals; or $R^{73}$ and $R^{74}$ together with the carbon atom to which they are attached form a $C_{3-7}$ spirocycloalkyl group optionally substituted by one or two methyl groups.

Preferred members according to formula (IV) are those wherein $R^{76}$, $R^{77}$ and $R^{78}$ are hydrogen; $R^{75}$ is hydrogen, methyl, phenyl or a heterocyclic radical; and $R^{73}$ and $R^{74}$ are independently methyl or trifluoromethyl, or when taken together with the carbon atom to which they are attached form a $C_5$ or $C_6$ cycloalkyl radical.

Oxime derivatives which are suitable for use as antidotes with herbicides are disclosed, for instance, in U.S. Pat. Nos. 4,070,389 and 4,269,775 and have the general formula

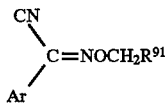

in which Ar is a phenyl or substituted phenyl radical where the substituents are optionally methyl, methoxy, chlorine, cyano or trifluoromethyl, or Ar is a naphthyl radical;

$R^{91}$ is cyano,

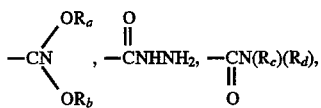

or —$CN(R_g)(R_h)$, where $R_a$ and $R_b$ are independently lower alkyl or together with the carbon form an oxygen or sulfur containing 5 - or 6-membered heterocyclic ring which is unsubstituted or substituted by lower alkyl, halogen and/or nitro; ($R_c$) and ($R_d$) are independently hydrogen, lower alkyl, cycloalkyl, which are unsubstituted or further substituted with one or more halogen, lower alkoxy and/or cyano; ($R_g$) and ($R_h$) together with the nitrogen form a 5- or 6-membered ring which is unsubstituted or mono- or polysubstituted by halogen, cyano and/or lower alkyl and which can be interrupted by a nitrogen, oxygen or sulfur atom. Representative compounds of this type are those in which $R^{91}$ is cyano, and in which $R^{91}$ is 1,3-dioxolan-2-yl. The latter compound has the chemical name O-[2-(1,3-dioxolanyl)methyl]-alpha-cyanobenzaldoxime.

Thiazole carboxylic acids and derivatives suitable for use as antidotes are disclosed generally in U.S. Pat. No. 4,199,506, and have the general formula

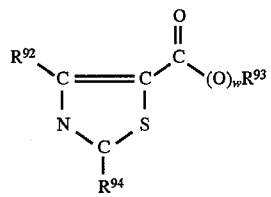

in which $R^{92}$ is alkyl, haloalkyl or trialkoxymethyl; $R^{93}$ is variously hydrogen, agriculturally acceptable cations or various hydrocarbyl or substituted hydrocarbyl moieties; w is 0 or 1; and $R^{94}$ is chloro, bromo, iodo, lower alkoxy or substituted or unsubstituted phenoxy. A representative member of this class is the compound benzyl-2-chloro-4-trifluoromethyl-methyl-5-thiazole carboxylate ($R^{92}$=trifluoromethyl; $R^{93}$=benzyl, $R^{94}$=chloro; w=1).

Another useful herbicide antidote compound is disclosed in European Patent No. 0104495 as having the formula

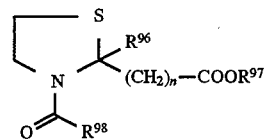

wherein $R^{98}$ is $C_1$–$C_3$ haloalkyl containing from 1 to 3 halogen atoms or a phenyl group optionally substituted; $R^{96}$ represents a hydrogen atom, a methyl or a phenyl; $R^{97}$ represents a hydrogen atom, a methyl or a phenyl; $R^{97}$ represents a $C_1$–$C_8$ alkyl group, a $C_5$–$C_6$ cycloalkyl group, a cyclohexylmethyl group, a phenyl group optionally substituted, a benzyl group optionally substituted, an allyl or propargyl group; and n is zero or one.

A representative antidote of that group would be:

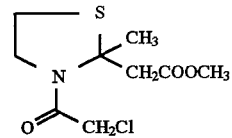

Especially preferred antidotes for use in the present invention include: 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-[3-(dichloroacetyl)-2,2-dimethyl-5-oxalidinyl]pyridine; 4-(dichloroacetyl)-1-oxa-4-azapiro-(4,5)-decane; 2,2-dichloro-1-(1, 2, 3, 4-tetrahydro-1-methyl-2-isoquinolyl)ethanone; cis/trans-1,4-bis(dichloroacetyl)-2,5-dimethylpiperazine; N-(dichloroacetyl)-1, 2, 3, 4-tetrahydroquinaldine; 1,5-bis(dichloroacetyl)-1,5-diazacyclononane; 1-(dichloroacetyl)-1-azaspiro[4,4]nonane; α-[(cyanomethoxy)imino]benzeneacetonitrile; α-[(1,3-dioxolan-2-ylmethoxy)imino]benzeneacetonitrile; O-[1,3-dioxolan-2-ylmethyl]-2,2,2-trifluoromethyl-4'-chloroacetophenone oxime; benzenemethamine, N-[4-(dichloromethylene)-1,3-diotholan-2-ylidene]-α-methyl;

hydrochloride; diphenylmethoxy acetic acid, methyl ester; 1,8-naphthalic anhydride;4,6-dichloro-2-phenylpyrimidine; 2-chloro-N-[1-(2, 4, 6-trimethylphenyl)ethenyl]-acetamide; cloquintocet; and ethylene glycol acetal of 1,1-dichloroacetone.

Herbicidal compositions according to this invention may also contain one or more additional pesticidally active ingredients. Herbicides which may be used as co-herbicides with 4-benzoylisoxazole or 2-cyano-1,3-dione compounds of formula (I) with benefit in combination with an antidote as described herein include, preferably, thiocarbamates (including dithiocarbamates), α-haloacetamides, heterocyclyl phenyl ethers, imidazolinones, pyridines and sulfonylureas. it is within the purview of this invention that other classes of herbicides, e.g., triazines, ureas, diphenyl ethers, nitroanilines, thiazoles, pyrrolidinones, aromatic and heterocyclic di- and triketones, etc., the individual members of which classes may be derivatives having one or more substituents selected from a wide variety of radicals may suitably be used a co-herbicides. Such combinations can be used to obtain selective weed control with low crop injury in several varieties of crop plants such as corn, grain sorghum, and cereals such as wheat, rice, barley, oats and rye, as well as several varieties of oil-seed crops such as soybeans and cotton. Insecticides, such as synthetic pyrethroids, and fungicides, such as carbamates and triazoles, may also be included in the herbicidal compositions of this invention.

Effective weed control coupled with low crop injury is a result of treatment of a plant locus with a combination of an herbicidal 4-benzoylisoxazole or 2-cyano-1,3-dione compound and an antidote compound in accordance with the present invention. By application to the "plant locus" is meant application to the plant growing medium, such as soil, as well as to the seeds, emerging seedlings, roots, stems, leaves, or other plant parts.

The phrase "combination of an herbicidal 4-benzoylisoxazole or 2-cyano-1,3-dione compound and an antidote compound" includes various methods of treatment. For example, the soil of a plant locus may be treated with a "tank-mix" composition containing a mixture of the herbicide and the antidote which is "in combination." Or, the soil may be treated with the herbicide and antidote compounds separately so that the "combination" is made on, or in, the soil. After such treatments if the soil with a mixture of herbicide and antidote or by separate or sequential application of the herbicide and the antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination." Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and an antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination." Or, the herbicide and antidote components in concentrated form may be in a mixture in a single container as a "combination." Either such a "combination" may be diluted or mixed with adjuvants suitable for soil applications. Another example of a commercially-presented combination is a container of antidote-coated crop seed sole, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of a particular 4-benzoylisoxazole or 2-cyano-1,3-dione herbicide to be applied to the plant locus or crop-growing area will vary with, inter alia, the nature of the weeds, the particular herbicide used, the time of application, the climate and the nature of the crop. Application rates of between about 0.01 kg/ha and 5.0 kg/ha of 4-benzoylisoxazole or 2-cyano-1,3-dione herbicide are generally suitable, with a rate of about 0.01 kg/ha to 4.0 kg/ha being preferred, and about 0.01 kg/ha to 2.0 kg/ha being especially preferred.

The amount of a given antidote to be utilized in combination with the herbicide according to this invention and the manner of its utilization and resulting efficacy can vary according to various parameters, such as the particular antidote to be employed, the crop which is to be protected, the amount or rate of herbicide to be applied, and the soil and climatic conditions of the agricultural environment in which the combination is to be applied. The selection of a specific antidote for use in the herbicide composition, the manner in which it is to be applied (e.g., tank-mix, in-furrow application, seed treatment, etc.), the determination of activity which is non-phytotoxic but antidotally-effective, and the amount necessary to provide this result, can be readily performed utilizing the test procedures in the cited patents, such as U.S. Pat. No. 4,021,224, in accordance with common practice in the art.

For other descriptions of antidotes and methods of their use, reference is made to U.S. Pat. No. 3,959,304; U.S. Pat. No. 3,989,503; U.S. Pat. No. 3,131,509; U.S. Pat. No. 3,564,768; U.S. Pat. No. 4,137,070; U.S. Pat. No. 4,294,764; U.S. Pat. No. 4,256,481; U.S. Pat. No. 4,415,353; and U.S. Pat. No. 4,415,352.

The antidote is applied in combination with the herbicide in a non-phytotoxic antidotally effective amount. By "non-phytotoxic" is meant an amount of the antidote which causes at most minor or no injury to the desired crop species. By "antidotally-effective" is meant an antidote used in an amount which is effective as an antidote with the herbicide to decrease the extent of injury caused by the herbicide to the desired crop species.

The ratio of herbicide to antidote may vary depending upon the crop to be protected, weed to be inhibited, herbicide used, etc., but normally an herbicide-to-antidote ratio ranging from 1:25 to 60:1 parts by weight may be employed, although much higher rates of antidote may be used, e.g., 1:100 to 1:300 parts by weight of herbicide to-antidote. The preferred weight ratio of herbicide-to-antidote is from about 1:10 to about 30:1. Another preferred weight ratio range is from about 1:1 to about 20:1, with an even more preferred weight ratio range being from about 2:1 to about 15:1.

In field applications, the herbicide, antidote, or a mixture thereof, may be applied to the plant locus without any adjuvants other than a solvent. Usually, the herbicide, antidote, or mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants These mixtures can be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of the herbicide, the application rate of the antidote, and the ratio of the herbicide-to-antidote application, as well as the nature of crops being tested, can affect the results of the test. Results may vary from crop to crop within the crop varieties.

EXAMPLES

The herbicide compound 5-cyclopropyl-4-[2-chloro-3-ethoxy-4-(ethylsulphonyl)benzoyl]-isoxazole ("Herbicide") and the antidote compound 2,2,5-trimethyl-N-dichloroacetyl oxazolidine ("Safener") were applied (at the rates listed in Table 1 below) preemergence to aluminum flats (measuring 9 wide×20 long×7 cm deep) containing pasteurized, sandy loam soil in which the following species had been sown: *Ipomoea hederacea* (ivyleaf morningglory) ("IPOHE"); *Setaria faberi* (giant foxtail) ("SETFA"); *Triticum aestivum* 'Prinqual' ("Wheat"); *Oryza sativa* 'Katy' ("Rice"); *Zea mays* 'Garst 8940' (corn) ("Corn GA8940"); and *Zea mays* 'Garst 8532' (corn) ("Corn GA8532"). The soil was fortified with fertilizer (10-10-10) prior to seeding. All of the compounds applied were technical grade materials. The compounds were dissolved in 50/50 acetone/water solution and applied with a carrier volume of 200 L/ha. All treatments were replicated two times.

After application, flats were placed in a greenhouse and maintained under good growing conditions. Injury to plants was evaluated 20 days after treatment ("DAT"). Injury was evaluated as percent control, with percent control being the total injury to the plants due to all factors including: inhibited emergence, stunting, malformation, albinism, chlorosis, and other types of plant injury. The control ratings range from 0 to 100 percent, where 0% represents no effect with growth equal to the untreated control and where 100% represents complete kill.

The results observed are summarized in Table 1 below.

TABLE 1

| Herbicide (g/ha) | Safener (g/ha) | IPOHE | SETFA | SORVU | Rice | Wheat | Corn GA8940 | Corn GA8532 |
|---|---|---|---|---|---|---|---|---|
| 125 | 0 | 90 | 95 | 98 | 75 | 0 | 3 | 3 |
| 250 | 0 | 98 | 100 | 99 | 78 | 0 | 53 | 45 |
| 500 | 0 | 100 | 100 | 100 | 85 | 0 | 85 | 85 |
| 125 | 250 | 93 | 93 | 95 | 70 | 0 | 0 | 0 |
| 250 | 250 | 98 | 99 | 100 | 85 | 0 | 0 | 0 |
| 500 | 250 | 100 | 100 | 98 | 90 | 10 | 8 | 18 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising:

(a) an herbicidally effective amount of an herbicidal 4-benzoylisoxazole compound, or an agriculturally acceptable salt thereof, of the formula

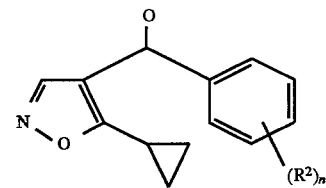

wherein:

each $R^2$ is independently selected from the group consisting of halogen, $C_1-C_4$ alkyl, $C_1-C_4$ alkoxy, $C_1-C_4$ haloalkyl, $-S(O)_pR^6$, and $-OSO_2R^7$, wherein $R^6$ is methyl or ethyl, p is zero, one or two, and $R^7$ is $C_1-C_4$ alkyl; and n is 2 or 3 and the benzoyl ring of said 4-benzoylisoxazole compound is 2,3-disubstituted, 2,4-disubstituted or 2,3,4-trisubstituted; and (b) an antidotally effective amount of an antidote compound which is antidotally effective for corn for said 4-benzoylisoxazole, said antidote compound being selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl), N-dichloroacetyl oxazolidine; N,N-diallyl dichloroacetamide; 2,2-dimethyl-N-dichloroacetyl oxazolidine; 4-(dichloroacetyl)-3,4-dihydro-3-methyl- 2H-1,4-benzoxazine; 3-[3-(dichloroacetyl)-2,2-dimethyl-5-oxalidinyl]pyridine; 4-(dichloroacetyl)-1-oxa-4-azaspiro-[4,5]-decane; 2,2-dichloro-1-(1, 2, 3, 4-tetrahydro-1-methyl-2-isoquinolyl)ethanone; cis/trans-1,4-bis(dichloroacetyl)-2, 5-dimethylpiperazine; N-(dichloroacetyl)-1, 2, 3, 4-tetrahydroquinaldine; 1,5-bis(dichloroacetyl)-1, 5-diazacyclononane; and 1-(dichloroacetyl)-1-azaspiro[4,4]-nonane.

2. A method of reducing injury to corn by a 4-benzoylisoxazole herbicide of the formula

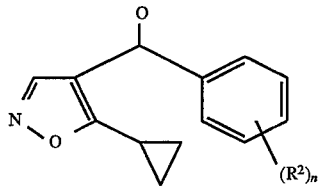

wherein:
each $R^2$ is independently selected from the group consisting of halogen, $C_1$–$C_4$ alkyl, $C_1$–$C_4$ alkoxy, $C_1$–$C_4$ haloalkyl, —S(O)$_p$R$^6$, and —OSO$_2$R$^7$, wherein R$^6$ is methyl or ethyl, p is zero, one or two, and $R^7$ is $C_1$–$C_4$ alkyl; and n is 2 or 3 and the benzoyl ring of said 4-benzoylisoxazole compound is 2,3-disubstituted, 2,4-disubstituted or 2,3,4-trisubstituted; which comprises applying to the soil, corn crop or seed a non-phytotoxic antidotally effective amount of an antidote compound which is antidotally effective for said 4-benzoylisoxazole herbicide, said antidote compound being selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-dimethyl-N-dichloroacetyl oxazolidine; 4-(dichloroacetyl)-3,4-dihydro-3-methyl-2H-1,4-benzoxazine; 3-[3-(dichloroacetyl)-2,2-dimethyl-5-oxalidinyl]pyridine; 4-(dichloroacetyl)-1-oxa-4-azaspiro-[4,5]-decane; 2,2-dichloro-1-(1, 2, 3, 4-tetrahydro-1-methyl-2-isoquinolyl)ethanone; cis/trans-1,4-bis(dichloroacetyl)-2, 5-dimethylpiperazine; N-(dichloroacetyl)-1, 2, 3, 4-tetrahydroquinaldine; 1,5-bis(dichloroacetyl)-1, 5-diazacyclononane; and 1-(dichloroacetyl)-1-azaspiro[4,4]nonane.

3. An herbicidal composition comprising:
(a) an herbicidally effective amount of an herbicidal 4-benzoylisoxazole selected from the group consisting of 5-cyclopropyl-4-[2-chloro-3-ethoxy-4-(ethylsulfonyl)benzoyl]isoxazole and 5-cyclopropyl-4-(2-methylsulfonyl-4-trifluoromethylbenzoyl)isoxazole, or an agriculturally acceptable salt thereof; and (b) an antidotally effective amount of an antidote compound which is antidotally effective for corn, said antidote compound being a member selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-[3-(dichloroacetyl)-2,2-dimethyl-5-oxalidinyl]pyridine; 4-(dichloroacetyl)- 1-oxa-4-azapiro-(4,5)-decane; 2,2-dichloro-1-(1, 2, 3, 4-tetrahydro-1-methyl-2-isoquinolyl)ethanone; cis/trans-1,4-bis(dichloroacetyl)-2, 5-dimethylpiperazine; N-(dichloroacetyl)-1, 2, 3, 4-tetrahydroquinaldine; 1,5-bis(dichloroacetyl)-1, 5-diazacyclononane; and 1-(dichloroacetyl)-1-azaspiro[4,4]nonane.

4. A method of reducing injury to corn by a 4-benzoylisoxazole herbicide selected from the group consisting of 5-cyclopropyl-4-[2-chloro-3-ethoxy-4-(ethylsulfonyl)-benzoyl]isoxazole and 5-cyclopropyl-4-(2-methylsulfonyl-4-trifluoromethylbenzoyl)-isoxazole, or an agriculturally acceptable salt thereof which possesses herbicidal properties, said method comprising applying to the soil, corn crop or seed a non-phytotoxic antidotally effective amount of an antidote compound which is antidotally effective for said 4-benzoylisoxizole, said antidote compound being selected from the group consisting of 2,2,5-trimethyl-N-dichloroacetyl oxazolidine; 2,2-dimethyl-5-phenyl-N-dichloroacetyl oxazolidine; 2,2-dimethyl-5-(2-furanyl)-N-dichloroacetyl oxazolidine; 2,2-dimethyl-5-(2-thienyl)-N-dichloroacetyl oxazolidine; N,N-diallyl dichloroacetamide; 2,2-spirocyclohexy-N-dichloroacetyl oxazolidine; 2,2-dimethyl-N-dichloroacetyl oxazolidine; 4-(dichloroacetyl)-3,4-dihydro-3-methyl-2H-1,4-benzoxazine; 3-[3-(dichloroacetyl)-2,2-dimethyl-5-oxalidinyl]pyridine; 4-(dichloroacetyl)-1-oxa-4-azapiro-(4,5)-decane; 2,2-dichloro-1-(1, 2, 3, 4-tetrahydro-1-methyl-2-isoquinolyl) ethanone; cis/trans-1,4-bis(dichloroacetyl)-2, 5-dimethylpiperazine; N-(dichloroacetyl)-1, 2, 3, 4-tetrahydroquinaldine; 1,5-bis(dichloroacetyl)-1, 5-diazacyclononane; and 1-(dichloroacetyl)-1-azaspiro[4,4] nonane.

* * * * *

UNITED STATES PATENT AND TRADEMARK OFFICE
CERTIFICATE OF CORRECTION

PATENT NO. : 5,627,131

DATED : May 6, 1997

INVENTOR(S) : John M. Shribbs, David L. Lee

It is certified that error appears in the above-identified patent and that said Letters Patent is hereby corrected as shown below:

Claim 1, column 14, lines 40-48, formula should appear as follows:

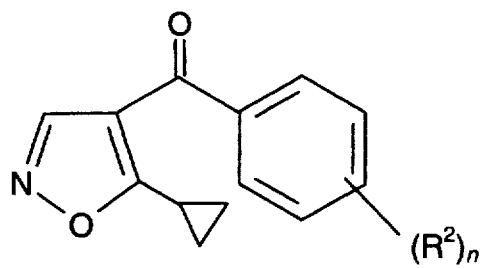

UNITED STATES PATENT AND TRADEMARK OFFICE
CERTIFICATE OF CORRECTION

PATENT NO. : 5,627,131
DATED : May 6, 1997
INVENTOR(S) : John M. Shribbs, David L. Lee It is certified that error appears in the above-indentified patent and that said Letters Patent is hereby corrected as shown below:

Claim 2, column 15, lines 11-19, formula should appear as follows:

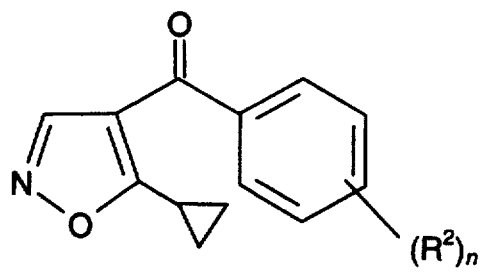

Signed and Sealed this

Twenty-first Day of October 1997

Attest:

BRUCE LEHMAN

Attesting Officer    Commissioner of Patents and Trademarks